United States Patent
Blei et al.

(10) Patent No.: US 10,071,205 B2
(45) Date of Patent: Sep. 11, 2018

(54) APPARATUS FOR DETERMINING INFORMATION ASSOCIATED WITH REFLECTION CHARACTERISTICS OF A SURFACE

(71) Applicant: SANOFI-AVENTIS DEUTSCHLAND GMBH, Frankfurt am Main (DE)

(72) Inventors: Gertrud Blei, Jena (DE); Gunter Heumann, Jena (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 15/315,621

(22) PCT Filed: Jun. 9, 2015

(86) PCT No.: PCT/EP2015/062766
§ 371 (c)(1),
(2) Date: Dec. 1, 2016

(87) PCT Pub. No.: WO2015/189170
PCT Pub. Date: Dec. 17, 2015

(65) Prior Publication Data
US 2017/0304545 A1    Oct. 26, 2017

(30) Foreign Application Priority Data
Jun. 10, 2014   (EP) .................................... 14171715

(51) Int. Cl.
*A61M 5/31*       (2006.01)
*G01N 21/55*      (2014.01)

(52) U.S. Cl.
CPC ............. *A61M 5/31* (2013.01); *G01N 21/55* (2013.01); *A61M 2005/3126* (2013.01);
(Continued)

(58) Field of Classification Search
CPC ............ A61M 5/31; A61M 2205/8206; A61M 2205/6081; A61M 2005/3126;
(Continued)

(56) References Cited

U.S. PATENT DOCUMENTS 6,172,824 B1 *  1/2001  Lehmann .................. G01J 3/42
                                                              356/300
6,331,276 B1 * 12/2001  Takei ...................... G01N 21/554
                                                             422/82.09
(Continued)

FOREIGN PATENT DOCUMENTS

| WO | WO 2011/117212 | 9/2011 |
| WO | WO 2014/023763 | 2/2014 |
| WO | WO 2014/037331 | 3/2014 |

OTHER PUBLICATIONS

International Search Report and Written Opinion in International Application No. PCT/EP2015/062766, dated Aug. 25, 2015, 10 pages.
(Continued)

Primary Examiner — Sang Nguyen
(74) Attorney, Agent, or Firm — Fish & Richardson P.C.

(57) ABSTRACT

Apparatus for determining information associated with reflection characteristics of a surface comprising a sensor (60) configured to generate sensor output dependent on an intensity of light incident on the sensor and having a field of view directed at an external surface (57) in use; an illumination source (58) configured to emit light onto the external surface in use; an optically transparent window (61) located such as to allow light to pass from the illumination source to the external surface and to allow light to pass to the sensor from the external surface in use; a light concentrator (66) fixed to or integral with the window, the light concentrator being configured to concentrate at least some light from the illumination source onto the external surface in use such that
(Continued)

the concentrated light may be reflected from the external surface onto the sensor via the window; and a processor (40) configured to use the sensor output to determine information associated with reflection characteristics of the external surface.

12 Claims, 8 Drawing Sheets

(52) U.S. Cl.
CPC ............... *A61M 2205/3306* (2013.01); *A61M 2205/3313* (2013.01); *A61M 2205/50* (2013.01); *A61M 2205/502* (2013.01); *A61M 2205/52* (2013.01); *A61M 2205/6081* (2013.01); *A61M 2205/8206* (2013.01); *G01N 2201/062* (2013.01); *G01N 2201/08* (2013.01)

(58) Field of Classification Search
CPC ........ A61M 2205/502; A61M 2205/50; G01N 21/55; G01N 2201/062; G01N 2201/08
See application file for complete search history.

(56) References Cited

U.S. PATENT DOCUMENTS

| | | | |
|---|---|---|---|
| 7,230,260 B1* | 6/2007 | Tarui | G01N 21/274 250/227.25 |
| 7,382,460 B2* | 6/2008 | Higashiisogawa | G01N 21/4738 356/445 |
| 7,697,141 B2* | 4/2010 | Jones | E21B 47/102 356/445 |
| 2003/0030813 A1* | 2/2003 | Martin | G01N 21/552 356/445 |
| 2009/0231590 A1* | 9/2009 | Naya | G01N 21/41 356/445 |
| 2010/0321696 A1* | 12/2010 | Malik | B01L 3/502715 356/432 |
| 2011/0310394 A1* | 12/2011 | Li | G01N 21/553 356/450 |
| 2013/0016346 A1 | 1/2013 | Romanovsky et al. | |
| 2013/0100453 A1* | 4/2013 | Harrison | G01N 21/55 356/445 |
| 2014/0354998 A1* | 12/2014 | Bock | A61M 5/31 356/445 |

OTHER PUBLICATIONS

International Preliminary Report on Patentability in International Application No. PCT/EP2015/062766, dated Dec. 15, 2016, 7 pages.

\* cited by examiner

APPARATUS FOR DETERMINING INFORMATION ASSOCIATED WITH REFLECTION CHARACTERISTICS OF A SURFACE

CROSS-REFERENCE TO RELATED APPLICATIONS

This application is a U.S. national stage application under 35 USC § 371 of International Application No. PCT/EP2015/062766, filed on Jun. 9, 2015, which claims priority to European Patent Application No. 14171715.7 filed on Jun. 10, 2014, the entire contents of which are incorporated herein by reference.

FIELD

An aspect of the present invention relates to an apparatus for determining information associated with reflection characteristics of a surface. The apparatus may be a supplemental device configured for attachment to an injection device, and the surface may comprise part of an injection device.

BACKGROUND

A variety of diseases exist which require regular treatment by injection of a medicament. Such injection can be performed by either medical personnel or by patients themselves. As an example, type-1 and type-2 diabetes can be treated by patients themselves by injection of insulin doses once or several times per day. It is known to couple a supplemental device to an insulin injection device for recording information about the doses that are administered. Supplemental devices may be used to record information about the various times at which insulin doses are administered and the quantity of insulin administered during each such dose.

Problems may arise however when a patient does not keep a record of what type of insulin they are using, and in more serious cases when a patient uses the wrong type of insulin. Aspects of the present invention address the foregoing.

Colour detection is disclosed in the prior art, for instance in WO2011/117212.

SUMMARY

According to an aspect of the present invention there is provided an apparatus comprising: a sensor configured to generate sensor output dependent on an intensity of light incident on the sensor and having a field of view directed at an external surface in use; an illumination source configured to emit light onto the external surface in use; an optically transparent window located such as to allow light to pass from the illumination source to the external surface and to allow light to pass to the sensor from the external surface in use; a light concentrator fixed to or integral with the window, the light concentrator being configured to concentrate at least some light from the illumination source onto the external surface in use such that the concentrated light may be reflected from the external surface onto the sensor via the window; and a processor configured to use the sensor output to determine information associated with reflection characteristics of the external surface.

Using a light concentrator in this manner may increase the intensity of light that can be reflected onto the sensor from an external surface under analysis, thereby likely increasing the reliability of the information obtained from analysis of the reflection characteristics of the surface. Furthermore, providing the light concentrator on the window may enable a more compact optical arrangement to be realised. Additionally, providing the light concentrator on the window may make it easier to arrange these two components relative to one another, thereby likely increasing the ease and speed with which the apparatus can be manufactured. In the arrangement that the light concentrator is integral with the window, it may be easier to manufacture the apparatus because the step of fixing the light concentrator and the window will not be required to be implemented.

The light concentrator may be configured such that in use at least some light from the illumination source is reflected or refracted by the light concentrator towards the external surface.

The light concentrator may be a light guide configured such that in use at least some light from the illumination source is internally reflected within the light guide towards the external surface.

This may increase the intensity of light that may be reflected onto the sensor from an external surface under analysis, thereby likely increasing the reliability of the information obtained from analysis of the reflection characteristics of the surface. Utilising the principle of total internal reflection may reduce the amount of light absorbed by the light concentrator.

The light concentrator may be a light guide and is configured such that in use at least some light from the illumination source is reflected from a boundary surface of the light guide towards the external surface.

The light concentrator may be a light guide comprising a plurality of surfaces from which light from the illumination source may be reflected towards the external surface.

The light concentrator may be at least partially prismatic in shape.

At least part of the light concentrator may have a substantially triangular shaped cross section.

The light concentrator may have an optical power and optionally may comprise a lens.

The apparatus may be a supplemental device configured for attachment to an injection device.

The aforementioned information may be a property of an injection device which comprises the external surface. Such information may be indicative of a type of medicament within an injection device which comprises the external surface. This may make it easier for a patient to maintain a log of the type of medicament they have been using. This may also be used to provide an indication that medicament within the injection device is not suitable for a patient using the injection device.

DETAILED DESCRIPTION OF PREFERRED EMBODIMENTS

In the following, embodiments of the present disclosure will be described in the context of a supplemental device for determining an amount of dose dialled, or an amount of dose dispensed, by an injection device. Such a supplemental device may be provided with optical character recognition (OCR) functionality for making such a determination. The present invention is however not limited to such application and may equally well be deployed with supplemental devices of other kinds, for example a supplemental device that merely displays a dialled dose amount in larger format than it appears on the number sleeve of an injection device.

Figure 1:
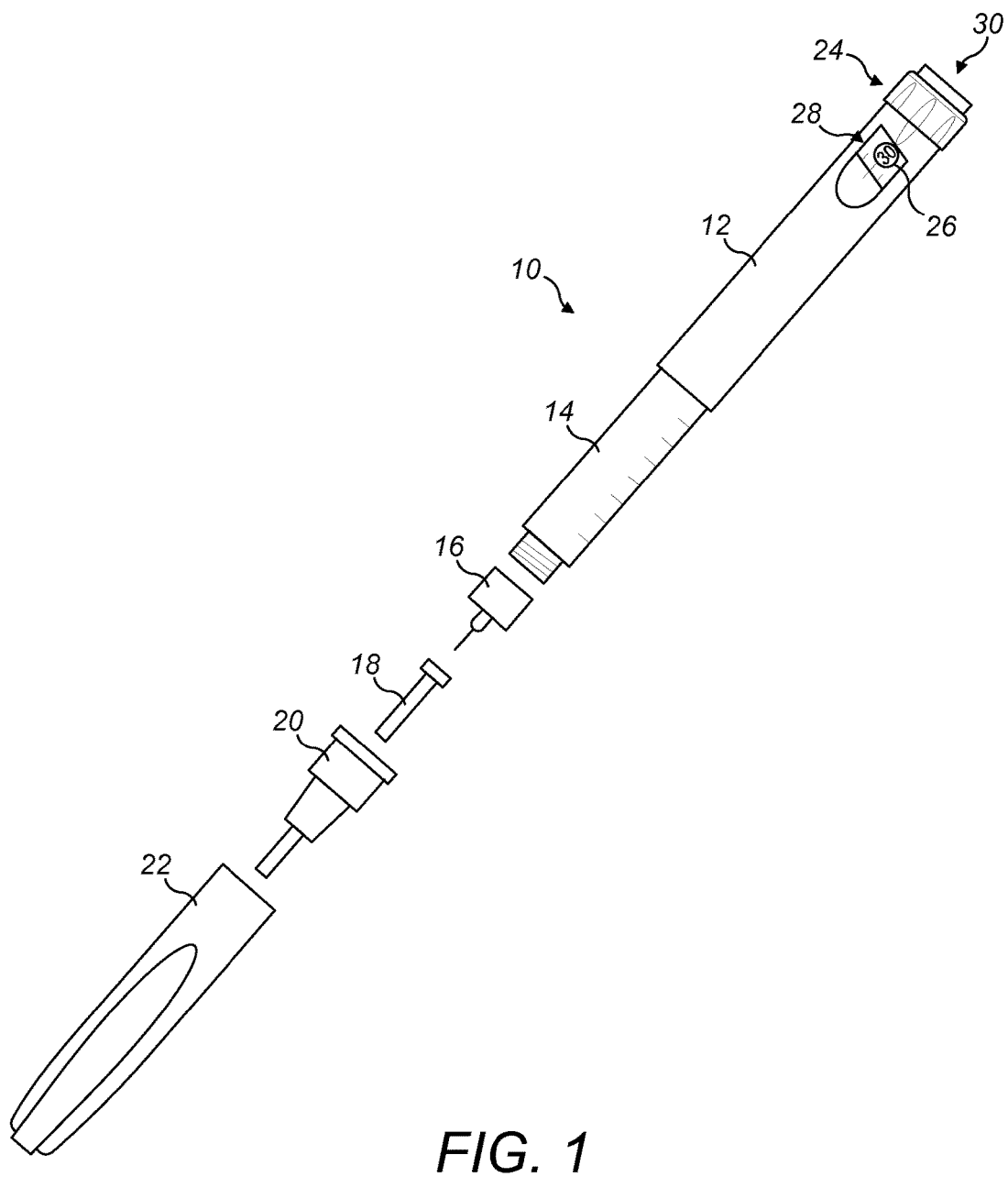
FIG. 1 is a schematic view of an exemplary injection device.

FIG. 1 is an exploded view of an injection device 10, which may for instance represent the Solostar™ injection pen sold by Sanofi.

The injection device 10 of FIG. 1 is a pre-filled, disposable injection pen that comprises a housing 12 and contains an insulin container 14, to which a needle 16 can be affixed. The needle 16 is protected by an inner needle cap 18 and an outer needle cap 20, which in turn can be covered by a cap 22. An insulin dose to be ejected from injection device 10 can be selected by turning the dosage knob 24 (this act may be referred to as dialling an insulin dose). A marker comprising a number 26 indicative of the selected dose (the dialled dose) is displayed via dosage window 28 in multiples of International Units (IU) for instance. An example of a dialled dose displayed in the dosage window 28 may be 30 IUs, as shown in FIG. 1.

The numbers 26 displayed in the dosage window 28 are printed on a sleeve (known as the number sleeve 17) contained in the housing 12 and which mechanically interacts with a piston inside the insulin container 14. When needle 16 is inserted into the skin of a patient and the injection button 30 is pushed, an amount of insulin corresponding to the dialled quantity displayed in the display window 28 is ejected from the injection device 10. During the course of the injection, as insulin leaves the injection device 10, the number sleeve 17 rotates. This causes the number 26 displayed in the dosage window 28 to change in accordance with the dialled amount of insulin yet to be dispensed. In other words, during the course of an injection the numbers 26 that successively align with the dosage window 28 are caused to count down.

Figure 2:
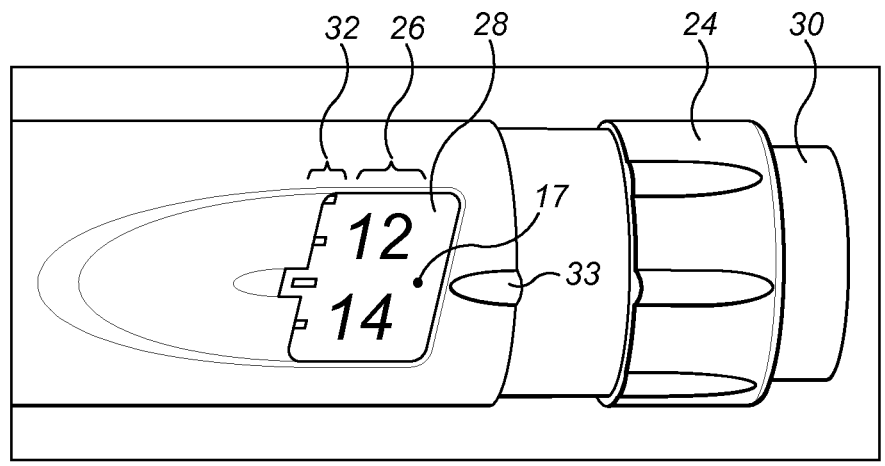
FIG. 2 is an enlarged view of an end of the injection device in FIG. 1.

FIG. 2 shows the dosage window 28 after 17 IUs of insulin have been delivered from the injection device 10 during the course of the injection in the preceding paragraph.

Figure 3:
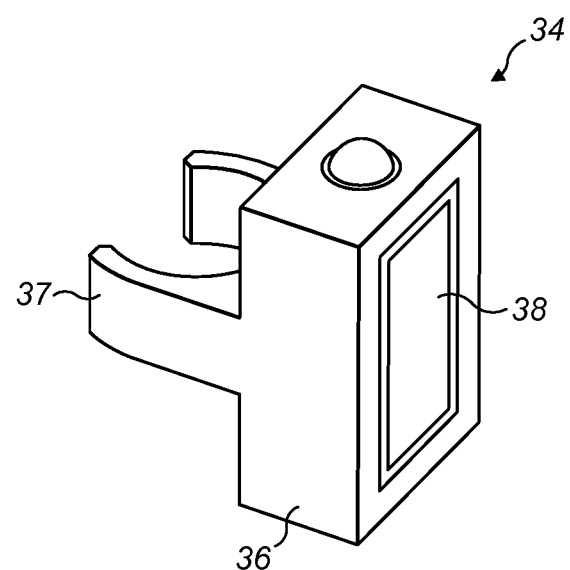
FIG. 3 is a schematic view of a supplemental device.

FIG. 3 is a schematic illustration of a supplemental device 34 which may be releasably attached to an injection device such as the one depicted in FIG. 1. The supplemental device 34 comprises a housing 36 which is provided with a mating unit, coupling unit or connector 37 for embracing the housing 12 of an injection device 10. In particular the connector 37 may be configured to snap-fit onto the housing 12 of an injection device 10 in such a way that the device 34 can be subsequently removed therefrom. The connector 37 need not however be of the snap-fit variety and other arrangements may alternatively be suitable for coupling the supplemental device 34 to an injection device.

Figure 4:
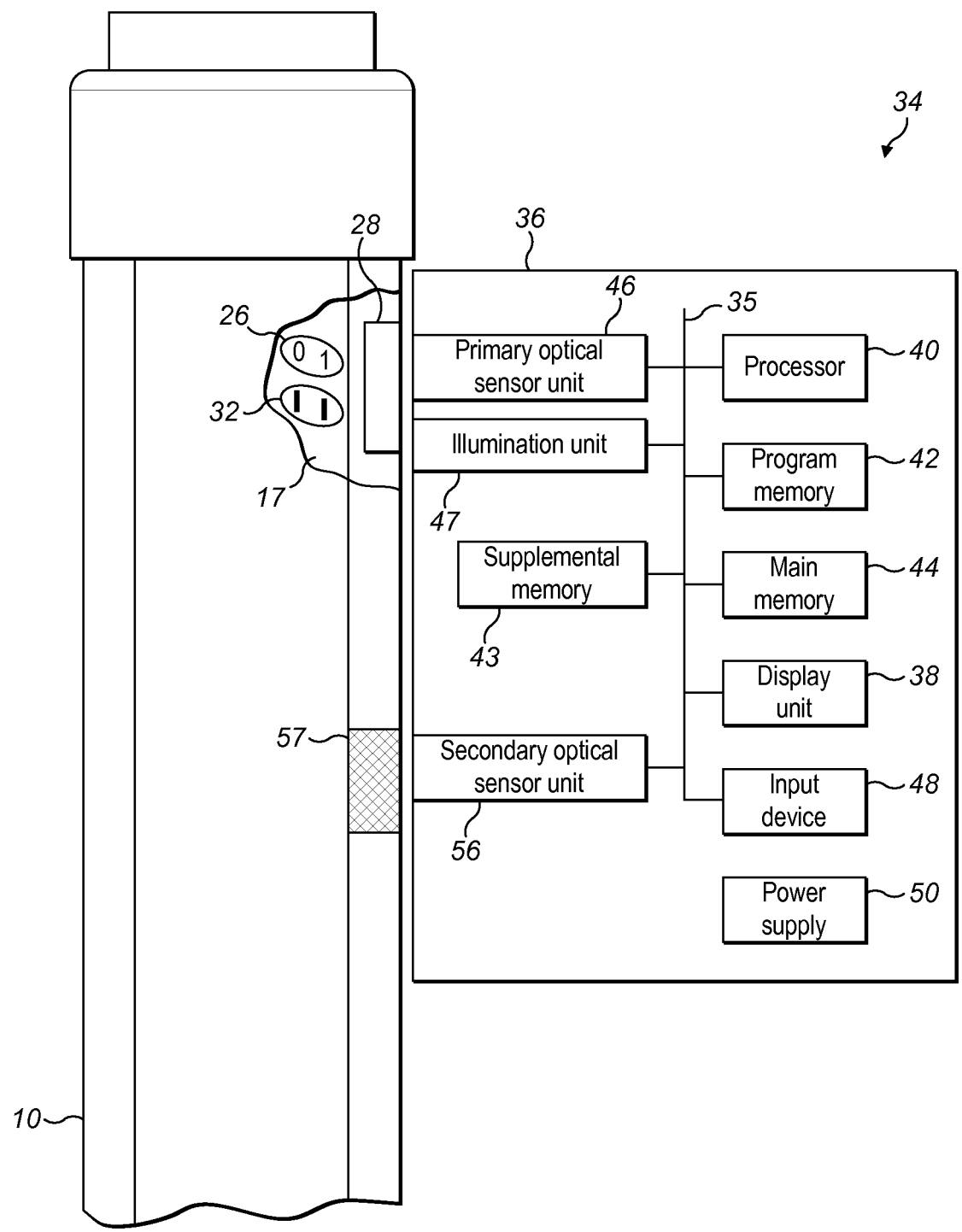
FIG. 4 is a schematic internal view of the supplemental device in FIG. 3.

When coupled to an injection device 10, the supplemental device 34 obstructs the dosage window 28 (as in FIG. 4). The supplemental device 34 contains at least one optical sensor for gathering information from the injection device 10. In particular the optical sensor(s) is(are) caused to gather information indicative of what is displayed in the dosage window 28. This gathered information is then capable of being processed for generating a dose history database.

Such a dose history database may include records containing information about the various times at which insulin doses are administered and the quantity of insulin administered during each dose. The gathered information may also be processed for the purpose of displaying numbers 26 aligned with the dosage window 28 in larger format, for example by displaying numbers on a display unit which are larger than those provided on the number sleeve 17. This improves the readability of the amount of dose dialled or, in the case of an injection, the dialled dose amount yet to be delivered.

FIG. 4 illustrates an internal schematic view of the supplemental device 34 in a state where it is coupled to an injection device 10.

Within the housing 36 of the supplemental device 34, a variety of components are located and coupled together by a system bus 35. One such component includes a processor 40. Program memory 42 and main memory 44 are also coupled to the system bus 35. The processor 40 executes program code (e.g. software or firmware) stored in the program memory 42 and uses the main memory 44 to store intermediate results. The supplemental device 34 also comprises a supplemental memory 43 for storing the aforementioned dose history database. Program memory 42 may for instance be non-volatile memory such as Read-Only Memory. Main memory 44 may for instance be a volatile memory such as Random Access Memory, DRAM or SDRAM and supplemental memory 43 may for instance be Flash memory or an EEPROM or may comprise a memory card coupled to the system bus 35 via an interface such as a USB-type connection.

A primary optical sensor unit 46, also coupled to the system bus 35, is used to generate signals containing information indicative of what is displayed in the dosage window 28. The processor 40 may use these signals to determine delivered doses and generate the dose history database. The processor 40 may achieve this by executing an optical character recognition application to determine, from signals sent by the primary optical sensor unit 46, which number(s) 26 is(are) aligned with the dosage window 28. On the basis of such information the processor 40 then determines how much insulin has been dialled or, in the case of an injection, the dialled amount of insulin that remains to be delivered (or has already been delivered during the course of the injection).

Other components which may be coupled to the system bus 35 include an illumination unit 47, a display unit 38 and an input device 48. Such an illumination unit 47 may include one or more LEDs and may be controlled by the processor 40 to illuminate information displayed in the dosage window 28. An input device 48 (for example, a keypad) may be utilised by a user to interact with the supplemental device 34. Such an input device 48 may for instance be used to select one or more options displayed on a display unit 38. In some embodiments a display unit 38 may be provided with touch-screen functionality thus enabling it to function as both an output device and the input device 48.

A power supply source 50 (for example a battery) is for powering the various components of the supplemental device 34.

In some embodiments, the primary optical sensor unit 46 may comprise a camera and the processor 40 may cause a display unit 38 to show information, e.g. images, that represent the number sleeve 17 as it appears in the field of view of the camera.

Regardless of the particular combination of features provided, a supplemental device 34 further comprises a secondary optical sensor unit 56 coupled to the system bus 35. The processor 40 uses the secondary optical sensor unit 56 to determine characteristics of a surface portion 57 located on an injection device 10. The surface portion 57 may comprise a part of a label or a part of the outer casing of the injection device 10 for instance. The surface portion 57 may thus be fixed, adhered or printed onto the injection device 10 or may comprise an integral part of the outer casing of the injection device 10. This is useful because injection devices 10 having different properties may be provided with different kinds of surface portions 57. In particular, injection devices 10 containing different types of medicament (e.g. different types of insulin) may have different coloured surface portions 57. A supplemental device 34 is thus able to determine what type of medicament an injection device 10 contains by analysing characteristics of its surface portion 57 or a part of the surface portion 57, for instance a part of a label that includes details of the injection device 10 such as brand information and/or contents information.

As will be explained in more detail below, the processor 40 causes the secondary optical sensor unit 56 to illuminate the surface portion 57 with light of different wavelengths. The secondary optical sensor unit 56 generates signals indicative of the intensity of light, of each respective wavelength, reflected by the surface portion 57. These signals are then used by the processor 40 to determine a parameter associated with the injection device 10 comprising the surface portion 57 under analysis, for instance a property of the injection device 10 e.g. contents information. This is enabled by the processor 40 comparing the reflection characteristics of the surface portion 57 with one or more records, each of which associates a different property of an injection device with a respective reflection response. Different coloured surface portions 57 reflect different amounts of light across a spectrum of different wavelengths. Thus by determining the reflection characteristics of a surface portion 57 having a particular colour, a property associated with that colour in one of the aforementioned records can be determined. An example of one such property may be an injection device type or a medicament type.

As already mentioned, an implementation of the present invention is to distinguish medical devices having different coloured surface portions 57, e.g. depending on the kind of medication they contain. The surface portions 57 could, for instance, be coloured differently depending on the type of insulin the respective devices contain.

For example, injection devices 10 containing short-acting insulin may be provided with a first coloured, e.g. red coloured, surface portion 57 whereas injection devices 10 containing long-acting insulin may be provided with a second coloured, e.g. blue coloured, surface portion 57. A first record which associates short-acting insulin with reflection characteristics of the first colour, the colour red in this example, and a second record which associates long-acting insulin with reflection characteristics of the second colour, the colour blue in this example, may be accessed by the processor 40 for determining what type of insulin is contained within a particular injection device 10. More specifically, the reflection characteristics of the surface portion 57 of a particular injection device 10 are compared with those in the foregoing records. This enables the processor 40 to determine what insulin type has been associated with the colour of the surface portion 57. If the surface portion 57 is blue, for instance, then the processor 40 determines that the injection device 10 contains long-acting insulin.

It will be appreciated that injection devices containing other types of insulin or other types of medicament may be provided with different coloured surface portions. Following on from the example in the foregoing paragraph such colours should be other than red or blue. Corresponding records associating reflection characteristics of the various surface portion colours with respective types of insulin or other medicament may be provided for enabling a processor to determine what substance is contained by an injection device upon analysing reflection characteristics of its surface portion (or a part thereof).

Figure 5:
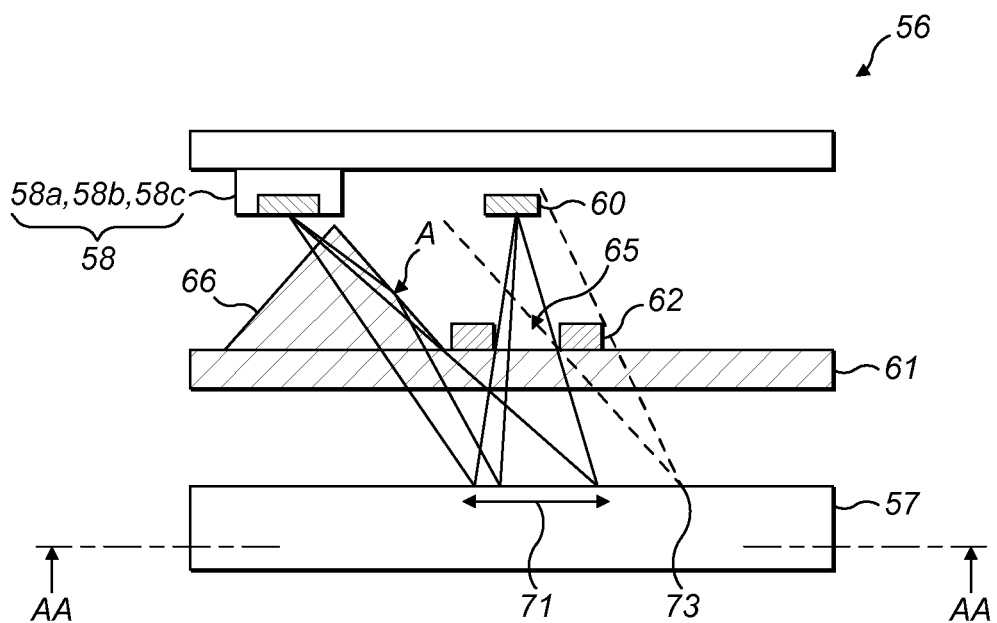
FIG. 5 is a schematic cross-sectional diagram of a secondary optical sensor unit according to one embodiment.

With reference to FIG. 5, the secondary optical sensor unit 56 will now be described in more detail. Briefly, the secondary optical sensor unit 56 comprises light sources 58 (otherwise referred to as illumination sources), a light guide 66, a sensor 60, a window 61 and a shield 62. The light sources 58 are configured to illuminate the surface portion 57 of an injection device 10 with light of different wavelengths, as aforementioned. The light guide 66 is configured to direct illumination from the light sources 58 onto the surface portion 57 under analysis. The sensor 60 is configured to measure the intensity of light reflected from the surface portion 57 and incident on the sensor 60. The window 61 is configured to protect internal components of the secondary optical sensor unit 56 from dirt ingress. The shield 62 is configured to restrict the amount of light which can be reflected from the surface portion 57 onto the sensor 60.

A fuller discussion of each of these components is now provided.

The plurality of light sources 58 may comprise LEDs for optically illuminating the surface portion 57 of an injection device 10 in use. Optical illumination, otherwise referred to herein as light, comprises electromagnetic radiation of a wavelength in the ultra violet, visible or infrared part of the electromagnetic spectrum. Ultraviolet light has a wavelength between approximately 10 nm and 400 nm for instance, visible light has a wavelength between approximately 400 nm and 750 nm for instance, and infrared light has a wavelength between approximately 750 nm and 1 mm for instance.

Each light source 58 may be configured to emit light of a different wavelength. For example the first, second and third light sources 58a, 58b, 58c in FIG. 5 are configured to emit first, second and third wavelengths $\lambda_1$, $\lambda_2$, $\lambda_3$ of light respectively. However, a plurality of light source groups may be provided instead, the light sources in each group being configured to emit light of the same wavelength.

Light of the first wavelength $\lambda_1$ emitted by the first light source 58a may be red, blue or green. Light of the second wavelength $\lambda_2$ emitted by the second light source 58b may be another of red, blue or green. Light of the third wavelength $\lambda_3$ emitted by the third light source 58c may be the remaining of red, blue or green.

In some embodiments, light of the first wavelength $\lambda_1$ is red, light of the second wavelength $\lambda_2$ is blue and light of the third wavelength $\lambda_3$ is green. Throughout this specification, red light has a wavelength between approximately 620 nm and 740 nm, blue light has a wavelength between approximately 450 nm and 495 nm and green light has a wavelength between approximately 520 nm and 570 nm.

The examples of the first to third wavelengths $\lambda_1$, $\lambda_2$, $\lambda_3$ of light outlined in the foregoing paragraph are merely exemplary. Such wavelengths of light may be of any value so long as they are different from one another. Additionally, the emissions of a light source 58a, 58b, 58c may not be solely at one discrete frequency but may instead be spread over a relatively narrow band of frequencies, which may overlap to some extent with the band of another light source 58a, 58b, 58c.

Referring again to FIG. 5, the sensor 60 is provided for generating sensor outputs. Such sensor outputs are indicative of the respective intensities of light of different wavelengths reflected from the surface portion 57. When the supplemental device 34 is coupled to an injection device 10, the surface portion 57 of the injection device 10 is located on an optical path with the sensor 60. In the example of FIG. 5 the optical path extends directly between the surface portion 57 and the sensor 60. Illumination from the light sources 58a, 58b, 58c is directed by the light guide 66 onto the surface portion 57 where it reflects prior to becoming incident on the sensor 60.

Following an exposure time, during which reflected light of a particular wavelength is incident on the sensor 60, the sensor 60 generates a signal indicative of the intensity of reflected light of that particular wavelength on the sensor 60 during that particular exposure time. In use, different wavelengths of light are caused to become incident on the sensor 60 for respective exposure times. The sensor 60 generates signals indicative of the intensity of reflected light of each particular wavelength on the sensor 60 during the respective exposure times.

In the example of FIG. 5, the processor 40 causes the first to third light sources 58a to 58c to respectively emit light of the first to third wavelengths $\lambda_1$ to $\lambda_3$ for respective exposure times $t_1$ to $t_3$. The light sources 58a to 58c are controlled to sequentially emit light of the first to third wavelengths $\lambda_1$ to $\lambda_3$. Therefore following a first exposure time $t_1$, during which reflected light of the first wavelength $\lambda_1$ is incident on the sensor 60, the sensor 60 generates a first signal S1 (described in the next paragraph). Following a second exposure time $t_2$, during which reflected light of the second wavelength $\lambda_2$ is incident on the sensor 60, the sensor 60 generates a second signal S2. Furthermore following a third exposure time $t_3$, during which light of the third wavelength $\lambda_3$ is incident on the sensor 60, the sensor 60 generates a third signal S3.

The first signal S1 mentioned in the foregoing paragraph is indicative of the intensity of reflected light of the first wavelength $\lambda_1$ incident on the sensor 60 during the first exposure time $t_1$. Similarly the second signal S2 is indicative of the intensity of reflected light of the second wavelength $\lambda_2$ incident on the sensor 60 during the second exposure time $t_2$. The third signal S3 is indicative of the intensity of reflected light of the third wavelength $\lambda_3$ incident on the sensor 60 during the third exposure time $t_3$.

A supplemental device 34 is calibrated (in a manner described below) such that if the surface portion 57 (or at least the part thereof from which light reflects onto the sensor 60) is a neutral colour (e.g. grey) then the respective signals generated by the sensor 60, in response to detecting light of the different wavelengths, are substantially similar. More specifically in such circumstances the respective signals generated by the sensor 60, which are indicative of the intensity of reflected light of each particular wavelength on the sensor 60 during the respective exposure times, are substantially similar.

In the example in FIG. 5, the supplemental device 34 is calibrated such that if the surface portion 57 (or at least the part thereof from which light reflects onto the sensor 60) is a neutral colour (e.g. grey) then the first to third signals S1 to S3 generated by the sensor 60 in use will be substantially similar. Such signals S1 to S3 are deemed to be substantially similar if they are indicative that during first to third exposure times $t_1$ to $t_3$ the intensity of reflected light of the first to third respective wavelengths $\lambda_1$ to $\lambda_3$ on the sensor 60 is substantially similar.

Calibrating a supplemental device 34 to perform in this manner involves altering the duration of one or more of the exposure times of light of the respective wavelengths (exposure times $t_1$ to $t_3$ in the example of FIG. 5). The respective durations of the calibrated exposure times are stored by the supplemental device 34, for example in the program memory 42. The supplemental device 34 utilises these calibrated exposure time durations when in use for the respective exposure times of light of different wavelengths. Advantageously, calibrating a supplemental device 34 in this way minimises the total amount of time for which the light sources 58 are activated in use. This reduces the power consumption of the supplemental device 34, thereby prolonging battery life.

Referring again to FIG. 5, as aforementioned the window 61 is provided for protecting internal components of the secondary optical sensor unit 56, such as the sensor 60, from ingress of contaminant materials. The window 61 is transparent to illumination emitted by the light sources 58. Therefore in FIG. 5 the window 61 is transparent to light of at least the first, second and third wavelengths $\lambda_1$, $\lambda_2$, $\lambda_3$. The window 61 is arranged such that when the supplemental device 34 is coupled to an injection device 10, the window 61 is located between the surface portion 57 of the injection device 10 and the other components of the secondary optical sensor unit 56. This can be achieved by axially offsetting the window 61 relative to the sensor 60 and light sources 58, thereby physically separating the sensor 60 and light sources 58 from the surface portion 57 of an injection device 10 in use.

It may be that the section of window 61, through which light reflected by the surface portion 57 travels on route to the sensor 60, has an optical power (focussing ability) of zero, though this is not strictly necessary. A window section having an optical power of zero does not cause light travelling through it to either converge or diverge. Although one or more lenses (not shown) may be provided for focussing light reflected by the surface portion 57 onto the sensor 60, this is not necessary and advantageously no such lenses are present in FIG. 5. As will become clear upon reading further, light that has not been emitted from the light sources 58 and then reflected from the surface portion 57 cannot influence signals generated by the sensor 60. In particular, a supplemental device 34 is configured such that, in use, only light that has been emitted by the light sources 58 and then reflected by the surface portion 57 (specifically, from the part thereof under analysis i.e. the part in the field of view of the sensor 60) is able to become incident on the sensor 60.

The shield 62, which can also be termed a screen, mask or a baffle, is co-located with the window 61 and may be provided thereon. The shield 62 is opaque to light of substantially all wavelengths detectable by the sensor 60. In particular the shield 62 is configured to substantially attenuate and thereby absorb light of these wavelengths. The shield 62 (or at least a surface thereof configured to face the surface portion 57 of an injection device 10, in use) may be coloured black and optionally may be matt, or in other words, substantially without a shine.

In view of the foregoing it will be appreciated that the shield 62 in FIG. 5 is opaque to light of the first, second and third wavelengths $\lambda_1, \lambda_2, \lambda_3$ and also light of substantially all other wavelengths detectable by the sensor 60.

The shield 62 restricts the amount of light which may be reflected from an injection device 10, to which the supplemental device 34 is coupled, onto the sensor 60. The shield 62 does this by defining an aperture 65. The aperture 65 is arranged such that, in use, it is located on an optical path between the surface portion 57 and the sensor 60. In FIG. 5, the optical path extends directly between the surface portion 57 and the sensor 60, and the aperture 65 is located on this optical path in the field of view of the sensor 60. The effect of the aperture 65 is that it restricts or limits the field of view of the sensor 60.

It will be appreciated that the field of view of the sensor 60 in FIG. 5, denoted 71, is defined by the aperture 65.

In some embodiments the centre of the aperture 65 may be substantially aligned with the centre of the field of view of the sensor 60.

As already mentioned, the light guide 66 is configured to direct illumination from the light sources 58 onto the surface portion 57 being analysed. Illumination from the light sources 58 is directed onto the surface portion 57 without first becoming incident on the sensor 60. In other words illumination from the light sources 58 does not become directly incident on the sensor 60, which provides that the light sources 58 are not in the field of view of the sensor 60. When the processor 40 causes the light sources 58 to emit illumination, only illumination that is reflected from the surface portion 57, along the optical path between the surface portion 57 and the sensor 60, is detected. This detected light travels through the aperture 65 when travelling along the optical path between the surface portion 57 and the sensor 60.

A light guide of the kind mentioned in the previous paragraph may comprise a triangular prism 66 such as that illustrated in FIG. 5 and may comprise optics grade glass or plastic for instance. The triangular prism 66 may be provided in contact with the window 61 and may be coupled thereto, for instance by adhering the two together. Alternatively however the triangular prism 66 may comprise an integral part of the window 61, the two being moulded as a single piece. In this configuration part of the window 61 is formed such that it performs the function of the triangular prism 66. In each of these configurations the light sources 58 are configured such that light from the light sources 58 is directed into the prism 66 which, for reasons elaborated on below, improves the efficiency of reflection characteristics analysis implementable by the supplemental device 34.

Total internal reflection of illumination from the light sources 58 within the triangular prism 66 increases the intensity of illumination incident on the part of the surface portion 57 from which it may reflect onto the sensor 60. For instance, in the illustration depicted in FIG. 5 illumination from the light sources 58 is reflected from prism-air boundaries due to total internal reflection, for instance the area denoted A, onto the surface portion 57 in the field of view 71 of the sensor 60. This advantageously improves both the efficiency and reliability of the reflection characteristics analysis implementable by the supplemental device 34 because a higher intensity of illumination from the light sources 58 becomes incident on the sensor 60.

The triangular prism 66 illustrated in FIG. 5 is arranged relative to the light sources 58 such that the side including the area denoted A is at an angle relative to the light sources 58. This angle is such that a beam of light from the light sources and incident on the side which includes the area denoted A is reflected from the prism-air boundary as it travels through the prism 66. One such beam of light that is reflected in this manner first travels from one of the light sources 58 to an air-prism boundary where it enters the prism 66 and is refracted thereby. The refracted beam of light then travels through the prism 66, for instance to the prism-air boundary area A. Since the orientation of this boundary is arranged relative to the light sources 58 such that total internal reflection can take place, the refracted beam of light totally internally reflects from this boundary back into the prism. The reflected light then leaves the prism 66, passes through the protection window 61, and is refracted again when it travels through the window-air boundary, whereby it becomes incident on the surface portion 57. More specifically the beam of light leaving the protection window 61 becomes incident on the part of the surface portion 57 from which it may reflect prior to being detected by the sensor 60.

Looking at FIG. 5, it is apparent that were the beam of light referred to above not reflected from the prism-air boundary area A, it would not have become incident on the part of the surface portion 57 in the field of view 71 of the sensor 60. Utilising the principle of total internal reflection in the above manner thereby increases the intensity of optical illumination from the illumination sources 58 that becomes incident on the surface portion 57 (in particular, the relevant area thereof). Put more simply, the prism 66 guides more light from the light sources 58 onto the surface portion 57 (or the relevant part the surface portion 57) than would otherwise become incident thereon were it not for the presence of the prism 66; the prism 66 thus concentrates light from the light sources 58 onto the surface portion 57.

Referring again to FIG. 5, beams of light from the illumination sources 58 that are not totally internally reflected within the triangular prism 66 first travel from one of the light sources 58 to an air-prism boundary where it enters the prism 66 and is refracted thereby. The light then travels through and leaves the prism 66, passes through the protection window 61, and is refracted again when it travels through the window-air boundary, whereby it becomes incident on the surface portion 57. More specifically this light becomes incident on the part of the surface portion 57 from which it may reflect prior to being detected by the sensor 60.

When a supplemental device 34 comprising the arrangement in FIG. 5 is in use, a surface portion 57 is caused to be aligned with both the aperture 65 and the sensor 60. This occurs when the connector 37 (see FIG. 3) is mated with (coupled to) an injection device 10. Such alignment provides that the surface portion 57 (or at least a section of the surface portion) is in the field of view of the sensor 60, in use.

The aperture 65 provides that only the relevant section of the surface portion 57 is in the field of view of the sensor 60, in use. Moreover, this is achieved without the use of any lens in the path between the sensor 60 and the relevant section of the surface portion 57 (although the absence of such a lens is not strictly essential). Put another way, a supplemental device 34 comprising the arrangement in FIG. 5 is provided with a lens-free path between the surface portion 57 of the injection device 10 and the sensor 60. Thus, the supplemental device 34 is absent of any component with optical power between the surface portion 57 of the injection device 10 and the sensor 60. In other words, the supplemental device 34 is absent of any component between the surface portion 57 of the injection device 10 and the sensor 60 that is capable of focussing light. Put yet another way, all transparent components between the surface portion 57 of the injection device 10 and the sensor 60 have an optical power (focussing ability) of zero, which gives rise to no convergence or divergence of light.

A supplemental device 34 may be configured to engage with an injection device 10 such that the surface portion 57 thereof is a relatively small distance away from the sensor 60. Moreover, the mating arrangement may be such that the distance is substantially constant when the supplemental device 34 is engaged with the injection device 10.

The area of a surface portion 57 that is capable of reflecting light onto the sensor 60 of a supplemental device 34 is defined by a number of factors, for instance the shape and size of the aperture 65, the location of the aperture 65 relative to the sensor 60, the size and shape of the active part of the sensor 60 and the distance between the surface portion 57 and the aperture 65. The various features may be configured to provide a region of approximately 0.5 mm square, for example, of the surface portion 57 from which light can be reflected onto the sensor 60 when the supplemental device 34 is properly engaged with an injection device 10. The various features may be configured such that the area of the surface portion 57 from which light can be reflected onto the sensor 60 is always within acceptable limits even if the separation between the relevant parts of the supplemental device 34 and the injection device 10 increases or decreases by a modest amount.

The light sources 58 and the triangular prism 66 in FIG. 5 may be configured to illuminate a greater area of the surface portion 57 than is capable of reflecting light onto the sensor 60 for all separations between the relevant parts of the supplemental device 34 and the injection device 10 within a modest amount of the intended separation.

The field of view of the senor 60 in FIG. 5 is denoted 71. Illumination from the light sources 58 that is directed onto the surface portion 57 in the field of view 71 may be reflected through the aperture 65 and onto the sensor 60. An area of the surface portion 57 which is not in the field of view of the sensor 60 is denoted 73. Light which reflects from this area 73 may travel through the aperture 65 but will not become incident on the sensor 60. Such light may come from an ambient light source external to the supplemental device 34, for instance. The shield 62 thus prevents ambient light (i.e. light that is not emitted by the light sources 58) effecting sensor outputs that are generated when an analysis of the reflection characteristics of a surface portion 57 (or the part thereof from which light may reflect onto the sensor 60) is taking place.

Figure 6:
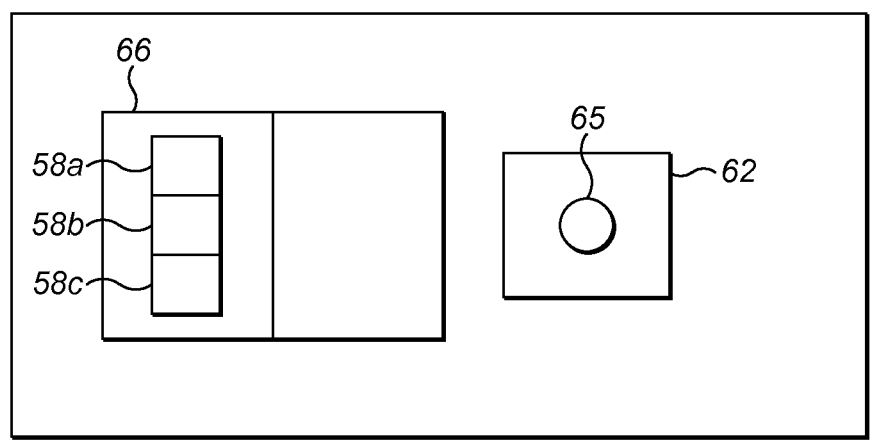
FIG. 6 is a schematic diagram of the underside of the secondary optical sensor unit in FIG. 5.

The structure of the shield 62 will now be explained in more detail with reference to FIG. 6. This figure shows an underside view of the secondary optical sensor unit 56 along the line AA in FIG. 5. It will be appreciated that the arrangement in FIG. 6 is viewable through the window 61 in FIG. 5. As already explained, the shield 62 limits or restricts the field of view of the sensor 60 and thereby limits or restricts the amount of light that can be reflected from the surface portion 57 onto the sensor 60 by preventing ambient light being reflected from the surface portion 57 onto the sensor 60 in use. Various ways of achieving this are envisaged.

The shield 62 may be applied, painted, printed, fixed or adhered to the window 61. For instance the shield 62 may comprise ink that has been applied to the window 61 in the desired shape. Alternatively the shield 62 may comprise a body of material (e.g. foil or plastic) that has been prepared (e.g. cut or injection moulded) into the desired shape, and then coupled to the window 61.

Figure 7:
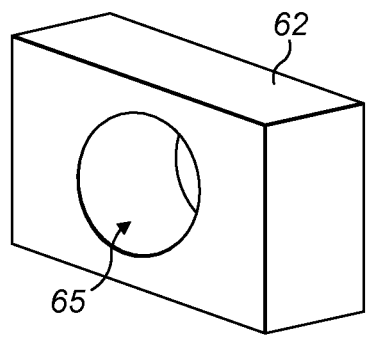
FIG. 7 is a schematic perspective view of the shield in FIGS. 5 and 6.

The shield 62 may be substantially flat. An example of such a shield 62 is depicted in FIG. 7 (although the thickness extending along the direction of the aperture 65 has been exaggerated for purposes of illustration). In its broadest sense the shield 62 in FIG. 7 comprises a body of material that is opaque to substantially all wavelengths of light detectable by the sensor 60, and which defines an aperture 65. In other words the shield 62 may be said to provide a mechanical mask which blocks light of substantially all wavelengths detectable by the sensor 60. The outer perimeter of the shield 62 need not necessarily be square-like and may comprise any other shape, for example a circle or other curved shape. The shield 62 may extend further on one side of the aperture 65 than the other. In other words, the aperture 65 need not necessarily extend through the centre of the shield body. Also, the aperture 65 need not necessarily be circular and may be any other shape, such as a square, provided that it achieves the function of limiting the field of view of the sensor 60, and thereby limiting the amount of light which can be reflected from the surface portion 57 onto the sensor 60 by preventing ambient light being reflected from the surface portion 57 onto the sensor 60 in use.

The shield 62 may be provided on the side of the window 61 nearest the sensor 60 although it may be provided on the side furthest from the sensor 60.

The shield 62 may be wholly or partially embedded in the window 61. In some embodiments the window 61 and the shield 62 may be integral. For instance the shield 62 may comprise a tinted section of the window 61.

Referring once again to FIG. 6, the respective light sources (e.g. those denoted 58a, 58b and 58c) may be arranged adjacent to one another for example in a line. The respective light sources may however be distributed around an axis extending through the aperture 65. For example one or more light sources may be located to the left of an axis extending through the aperture 65 towards the sensor 60 and one or more other light sources may be located to the right of such an axis. Also, in some embodiments light sources may be arranged in a ring, square, rectangle or triangle around such an axis.

How the secondary optical sensor unit 56 is used by the processor 40 to determine a property of an injection device 10 will now be explained with particular reference to the example in FIG. 5. The processor 40 controls the first, second and third light sources 58a, 58b, 58c sequentially to illuminate the surface portion 57 with light of first, second and third wavelengths $\lambda_1$, $\lambda_2$, $\lambda_3$ respectively for respective calibrated exposure times $t_1$, $t_2$, $t_3$. Upon such illumination the sensor 60 generates first, second and third signals S1, S2 and S3 respectively. These first to third signals S1 to S3 are (as aforementioned) indicative of the intensity of reflected light incident on the sensor 60 during the respective exposure times.

The processor 40 uses the first to third signals S1 to S3 to obtain first to third respective values A to C. In other words, the processor 40 assigns a numerical value to each of the first to third signals S1 to S3. The respective magnitudes of the first to third values A to C are proportional to a property of the first to third respective signals S1 to S3 that changes in accordance with the intensity of reflected light incident on the sensor 60 during a particular exposure time.

In the example that the sensor 60 is a photodiode for instance, the magnitude of an output voltage signal generated by the photodiode depends on the intensity of incident light during a particular exposure time. Thus when light of the first wavelength $\lambda_1$ for example is incident on the photodiode for an exposure time $t_1$, if the magnitude of the output voltage signal S1 is low then the corresponding first value A obtained by the processor 40 will be low also. However if the magnitude of the output voltage signal S1 generated is higher due to an increased intensity of light of the first wavelength $\lambda_1$ during the exposure time $t_1$, then the first value A obtained by the processor 40 will also be higher. The same applies in respect of the second and third values B and C obtained using second and third output voltage signals S2 and S3 generated when the photodiode is illuminated with light of the second and third wavelengths $\lambda_2$ and $\lambda_3$ respectively.

The first to third values A to C might be indicative of power per unit area (W/m$^2$). The first value A might be indicative of the power per unit area of light of the first wavelength $\lambda_1$ on the sensor 60 during a first exposure time $t_1$. Similarly the second and third values B and C might be indicative of the power per unit area of light of the second and third respective wavelengths $\lambda_2$ and $\lambda_3$ on the sensor 60 during second and third respective exposure times $t_2$ and $t_3$. The first to third values A to C might not however be indicative of power per unit area and might instead be indicative of another quantity, provided that the first to third values A to C are indicative of the same quantity. For example the first to third values A to C may be indicative of the total amount of electromagnetic energy (Joules) incident on the sensor 60 during respective exposure times $t_1$ to $t_3$.

The processor 40 performs a calculation using the first and second values A and B to provide a fourth value D. The processor 40 does not use the third value C when performing this calculation. Calculating the value of D comprises determining the output of a function f(A, B). Thus mathematically f(A, B)=D, wherein f(A, B) may comprise at least a division in which A is in the numerator and B is in the denominator. For example calculating the value of D may involve determining at least the value of NB or A/(A+B).

The processor 40 also performs another calculation in which the third value C is used to provide a fifth value E. Calculating the value of E comprises determining the output of a function f(C). Thus mathematically f(C)=E, wherein f(C) comprises one or more calibration factors which will be discussed later.

Having determined the fourth and fifth values D and E the processor 40 determines a property of the injection device 10 it is analysing. This is enabled by the processor 40 comparing the determined fourth and fifth values D and E with a list of records. These records respectively associate different information with different combinations of predetermined fourth and fifth values D and E.

The predetermined fourth and fifth values D and E in a particular record are those that the processor 40 determines if the surface portion 57 of an injection device 10 (or at least the part thereof from which light reflects onto the sensor 60) is a particular colour. This is how providing an injection device 10 with a surface portion 57 of a particular colour enables a supplemental device 34 to determine a property of the injection device 10. More specifically, providing the surface portion 57 with a particular colour results in the processor 40 determining a particular combination of fourth and fifth values D and E that are only determined when the analysed surface portion 57 is that particular colour. Comparing these values with the one or more records accessible by the processor 40 enables the processor to determine which parameter (e.g. which particular property of an injection device) has been associated with those particular fourth and fifth values D and E.

In practice, providing the surface portion 57 of an injection device with a particular colour may not result in the processor 40 determining particular fourth and fifth values D and E exactly. Instead, such values may only be determined within a range of accuracy that is influenced by the manufacturing tolerances of the supplemental device assembly process, and also, the efficiency of the various components thereof for example the sensor 60 and light sources 58. As such the records previously mentioned may associate predetermined ranges of fourth and fifth values D and E with particular parameters e.g. injection device properties, instead of associating exact values with injection device properties.

It will be appreciated that information indicative of different injection device types may be included in respective records. In other words, different injection device types may be associated with different combinations of predetermined fourth and fifth values D and E (or ranges thereof). In this implementation, different types of injection devices 10 may be provided with different coloured surface portions 57 for enabling a supplemental device 34 to determine the type of injection device 10.

It will also be appreciated that information indicative of different types of medicament (e.g. different types of insulin) may be included in respective records. In other words, different types of medicament may be associated with different combinations of predetermined fourth and fifth values D and E (or ranges thereof). In this implementation, injection devices 10 may be provided with different coloured surface portions 57 for enabling a supplemental device 34 to determine the type of medicament contained within the injection device.

Information concerning the type of medicament which a person injects themselves with may be stored in the aforementioned dose history database. Also, a supplemental device 34 may be configured to alert a user when an injection device 10 is determined to contain other than a pre-specified type of medicament. Such an alert may comprise the sounding on an audible alarm or the presentation of a visual indication on a display unit.

Figure 8:
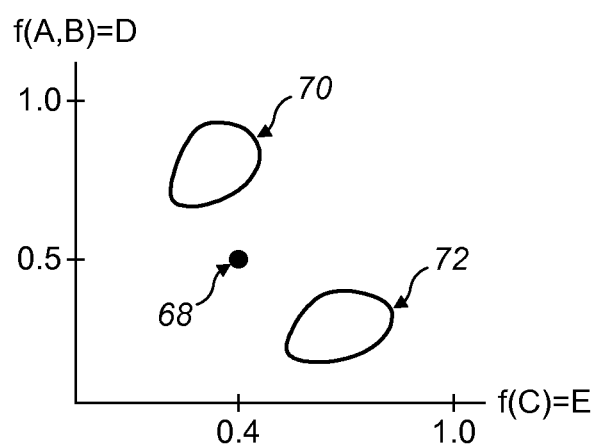
FIG. 8 is a graphical representation of fourth and fifth values that may be determined by a supplemental device.

FIG. 8 is a graphical representation of the foregoing. The vertical axis represents possible magnitudes of the fourth value D, which is the output of the function f(A, B). The horizontal axis represents the possible magnitudes of the fifth value E, which is the output of the function f(C). Since different coloured surface portions 57 are associated with different fourth and fifth values D and E, different coloured surface portions 57 are associated with different locations in the space shown in FIG. 8.

In the previous discussion regarding records it was stated that respective records may associate predetermined ranges of fourth and fifth values D and E with particular injection device properties. This is represented graphically in FIG. 8. For example, if the location associated with a particular coloured surface portion 57 is determined to be in the area 70 then the injection device 10 having that surface portion 57 is determined to have a particular property. However, if the location associated with a particular coloured surface portion 57 is determined to be in the area 72 then the injection device 10 having that surface portion 57 is determined to have another property.

The shape of an area associated with a particular property, such as those denoted 70 and 72 in FIG. 8, may define any shape. For instance one or more of the areas 70, 72 in FIG.

8 could define a square, rectangle, polygon, circle or oval for instance. Consider the example in which an area defines a square that extends between 0.9 and 1.0 on both the vertical and horizontal axes in FIG. 8. In this example the combination of D=0.9 to 1.0 and E=0.9 to 1.0 is associated with short-acting insulin. If the respective fourth and fifth values D and E of a particular surface portion 57 are each determined to be within the range 0.9 to 1.0, then the injection device 10 having that surface portion is determined to contain short-acting insulin.

Further configuration of a supplemental device 34 is required such that different supplemental devices 34 determine substantially similar fourth and fifth values D and E for a surface portion 57 having the same reflective properties, for instance a surface portion of the same colour. Graphically this means that further configuration is required such that different supplemental devices 34 determine surface portions 57 having the same reflective properties, for instance surface portions 57 of the same colour, to be associated with substantially similar locations in FIG. 8.

How such configuration is achieved will now be explained. A supplemental device 34 is configured such that if the surface portion 57 is a neutral colour (e.g. grey), the processor 40 determines the fourth and fifth values D and E to have predetermined magnitudes. The same occurs provided at least the part of the surface portion 57, from which light reflects onto the sensor 60, is neutral in colour.

The function f(A, B) used to determine the fourth value D may be such that the possible values of D range between 0 and 1. This function f(A, B) may also be such that if the surface portion 57 (specifically the part thereof from which light reflects onto the sensor 60) is a neutral colour (e.g. grey) the value of D is determined to be substantially 0.5.

A neutral coloured surface portion, for example a particular shade of grey, may have a reflectance of approximately 40% across all spectral ranges. In the foregoing example where the function f(A, B) comprises A/(A+B) the values of A and B will be substantially the same if the surface portion 57 is this colour. This is because (as already mentioned) the respective magnitudes of the first to third values A to C are proportional to a property of the first to third respective signals S1 to S3 that changes in accordance with the intensity of reflected light incident on the sensor 60 during a particular exposure time. Thus if the reflectance of the surface portion 57 is approximately 40% for light of the first to third wavelengths $\lambda_1$ to $\lambda_3$ then the respective values of A to C will be substantially similar. This provides that the fourth value D determined by calculating A/(A+B) will be substantially 0.5. Advantageously, if the function f(A, B) comprises A/(A+B) this minimises the effects of temperature drift imparted by the first light source 58a that emits light of the first wavelength for $\lambda_1$ for generating the first value A. This can be particularly useful where the first light source 58a is a red LED, because red LEDs are generally more susceptible to temperature drift than LEDs of colours such as blue and green.

The function f(C) used to determine the fifth value E may be such that the possible values of E also range between 0 and 1. For a neutral coloured surface having a reflectance of approximately 40% across all spectral ranges, the reflectance of light of the third wavelength $\lambda_3$ used to obtain the third value C will be 40% if the surface portion 57 (or at least the part thereof from which light reflects onto the sensor 60) is this colour. Such a colour may be the particular shade of grey mentioned in the previous paragraph. Calibration factors in the function f(C) may be set such that in this situation the value of E output from the function f(C) is substantially 0.4. These calibration factors are stored by the supplemental device 34, in the program memory 42 for example.

Consider a scenario in which a supplemental device 34 is calibrated in accordance with the previous two paragraphs. Such calibrated supplemental device 34, when coupled to an injection device 10 having a surface portion 57 that is of a shade of grey with a reflectance of approximately 40% across all spectral ranges, will determine the fourth and fifth values D and E to be those associated with the calibration location denoted 68 in FIG. 8.

In view of the foregoing it will be appreciated that in determining a property of an injection device 10 based on reflection characteristics of a surface portion 57, a supplemental device 34 could also utilise a three dimensional system which comprises two colour parameters D1 and D2 and one brightness parameter E. The two colour parameters D1 and D2 will be calculated as a function of (A, B, C). For example, D1=A/(A+B+C) and D2=B/(A+B+C). The brightness parameter E will be calculated similar to the foregoing as a function of C, E=f(C).

The heretofore described operation of the second optical sensor unit 56 is realised by the processor 40 operating in accordance with instructions contained in an operation application stored in the program memory 42. Relevant calibration information such as the calibrated exposure times (e.g. $t_1$ to $t_3$) and the aforementioned calibration factors may be accessed by the processor 40 operating in accordance with instructions contained in the operation application.

It will be appreciated that the above described embodiments are purely illustrative and are not limiting on the scope of the invention. Some other variations and modifications will now be discussed.

The heretofore described light guide need not necessarily comprise a triangular prism 66. For instance the light guide may comprise a prism 66 having another cross sectional shape, for instance a cross section having substantially the shape illustrated in FIG. 9. Total internal reflection of illumination from the light sources 58 within the prism 66 increases the intensity of illumination incident on the surface portion 57 in the field of view 71 of the sensor 60. For instance, in the illustration depicted in FIG. 9 illumination from the light sources 58 is reflected from prism-air boundaries A and B (due to total internal reflection) onto the surface portion 57 in the field of view 71 of the sensor 60.

Figure 9:
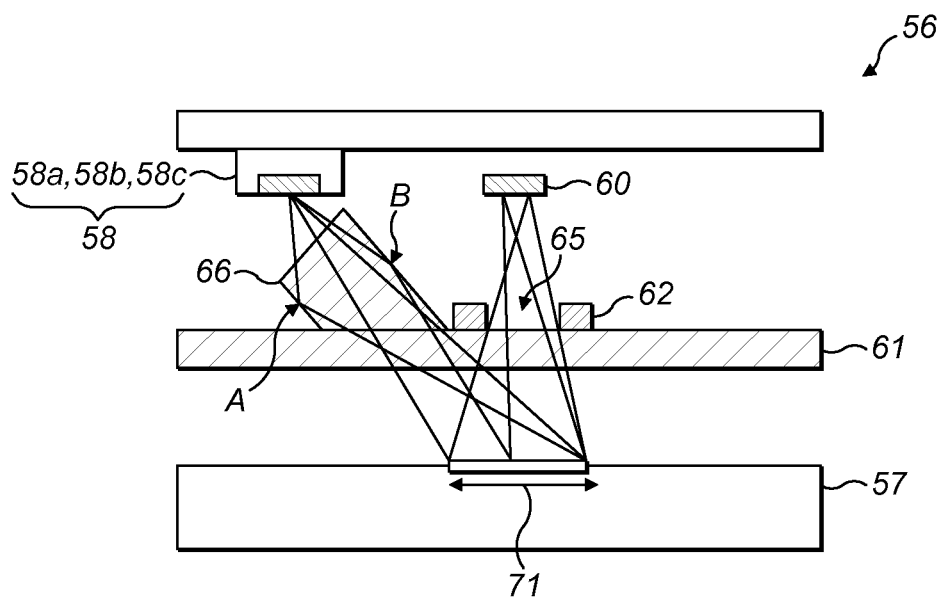
FIGS. 9 to 12 are schematic cross-sectional diagrams of a secondary optical sensor units according to respective further embodiments.

The prism 66 illustrated in FIG. 9 is arranged relative to the light sources 58 such that the side including the area denoted A, and also the side including the area denoted B, is at an angle relative to the light sources. The angle of each respective side is such that a beam of light from the light sources 58 and incident on either of the sides that include the areas denoted A or B is reflected from the prism-air boundary as it travels through the prism 66. One such beam of light that is reflected in this manner first travels from one of the light sources 58 to an air-prism boundary where it enters the prism 66 and is refracted thereby. The refracted beam of light then travels through the prism 66, for instance to either the prism-air boundary area A, or the prism-air boundary area B. Since the orientation of each of these boundaries is arranged relative to the light sources 58 such that total internal reflection may take place, the refracted beam of light totally internally reflects from the prism-air boundary on which it becomes incident back into the prism 66. The reflected light then leaves the prism 66, passes through the protection window 61, and is refracted again when it travels through the window-air boundary, whereby it becomes incident on the surface portion 57. More specifically the beam of light leaving the protection window 61 becomes incident on the part of the surface portion 57 from which it may reflect prior to being detected by the sensor 60.

Looking again FIG. 9, it is apparent that were the above mentioned beams of light not reflected from the prism-air boundary area A, or the prism-air boundary area B, they would not have become incident on the part of the surface portion 57 in the field of view 71 of the sensor 60. Utilising the principle of total internal reflection in the above manner thereby increases the intensity of optical illumination from the light sources 58 incident on the surface portion 71 (in particular, the relevant area thereof). Put more simply, the prism 66 guides more light from the light sources 58 onto the surface portion 57 (specifically the relevant part of the surface portion 57) than would otherwise become incident thereon were it not for the presence of the prism 66.

Where the term prism is used in this description, the object comprising the prism need not necessarily be prismatic as such, in other words it need not be solely prismatic (i.e. entirely the shape of a prism). Instead the term prism is also used in the context of objects having only a section that is prismatic, wherein this prismatic section is the part thereof being referred to when the term prism is used.

Upon reading this disclosure various other configurations and cross sectional shapes of light guides, in addition to those illustrated in FIGS. 5 and 9, will be apparent to persons skilled in the art. These various other light guide configurations also utilise the principle of total internal reflection, in addition to refraction, to direct illumination from the light sources 58 onto the surface portion 57 in the field of view 71 of the sensor 60. It is noted that such light guides need not necessarily be wholly or partially prismatic. They may also be provided in contact with the window 61 or may comprise an integral part thereof, the two being moulded as a single piece.

Figure 13:
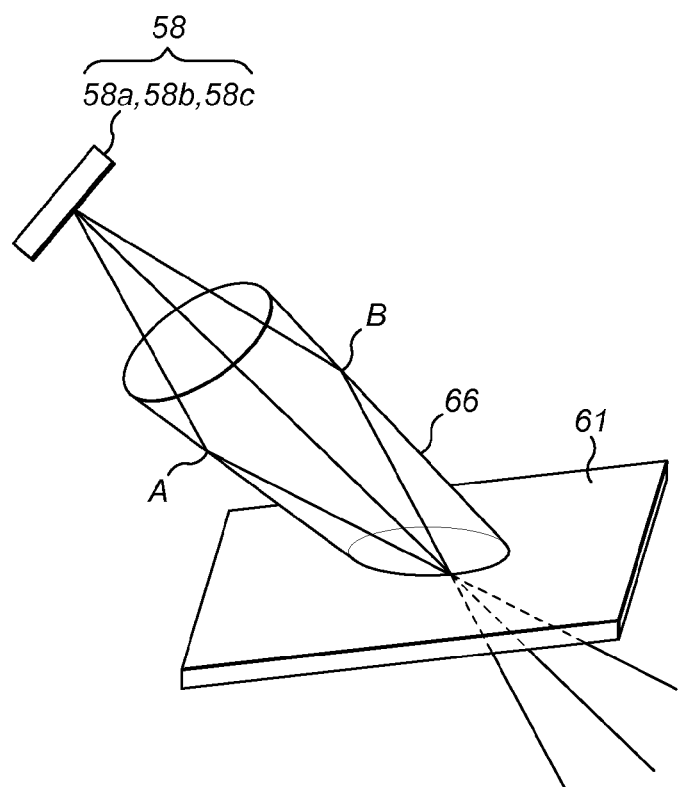
FIGS. 13 and 14 are schematic perspective views of light guides according to different embodiments.

The light guide arrangement illustrated in FIG. 13 comprises a substantially conical shape (and in some embodiments may change in cross sectional width along its length). In view of the forgoing disclosure it will be understood that light from the light sources 58 may be totally internally reflected within the light guide 66, for instance from the light guide-air boundaries denoted A and B at least.

Figure 14:
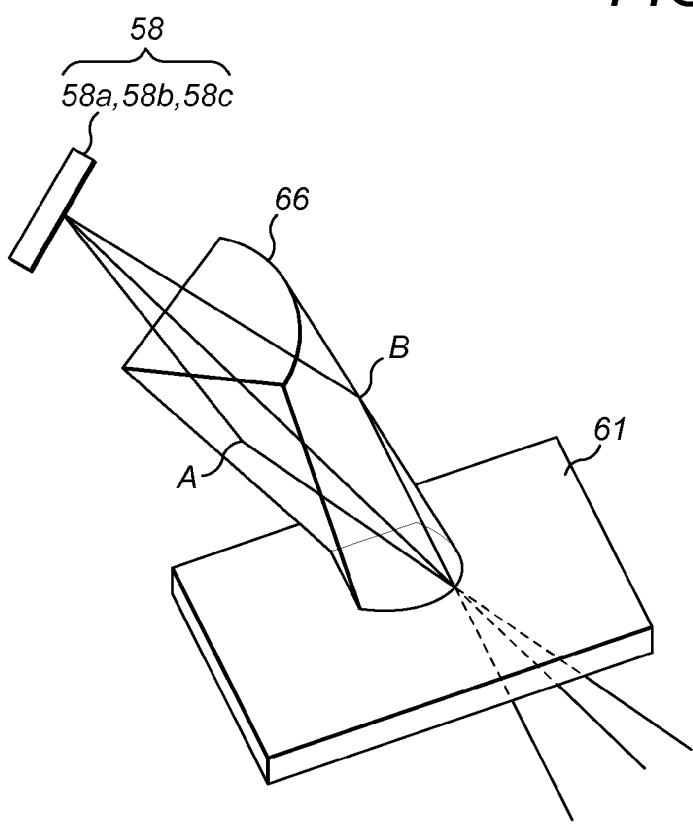

Another example of a suitable light guide 66 is illustrated in FIG. 14 which comprises both flat and curved surfaces. Again, in view of the forgoing disclosure it will be understood that light from the light sources 58 may be totally internally reflected within the light guide 66, for instance from the light guide-air boundaries denoted A and B at least.

Light guides need not necessarily rely on total internal reflection to increase the amount of light from the light sources 58 that is directed onto the surface portion 57 in the field of view 71 of the sensor 60. Some light guides may for instance be configured to achieve this effect by relying solely on the occurrence of refraction. More specifically such light guides only rely on the principle of refraction to guide light from the light sources 58 towards the relevant part of the surface portion 57 as it enters and leaves the light guide/window arrangement (which has a refractive index greater than that of air). For such light guides, at least some of the light guide-air boundaries are opaque to light from the light sources 58 by being coloured black for example; thereby providing that light from the light sources 58 cannot enter the sensor 60 without having been reflected from the surface 57 in use. Light impacting on such opaque surfaces within a light guide is thus absorbed.

Further variations and modifications will now be discussed.

One way of calibrating a supplemental device 34 has already been described, principally by altering the duration of one or more of the exposure times of light of the respective wavelengths (exposure times $t_1$ to $t_3$). However calibrating a supplemental device 34 may alternatively involve adding or subtracting a factor to/from each of the values A to C such that the resulting values are substantially similar when the surface portion 57 being analysed is a neutral colour (e.g. grey). These respective factors are stored by the supplemental device 34, for example in the program memory 42 and are added or subtracted to/from the values A to C in use.

Figure 10:
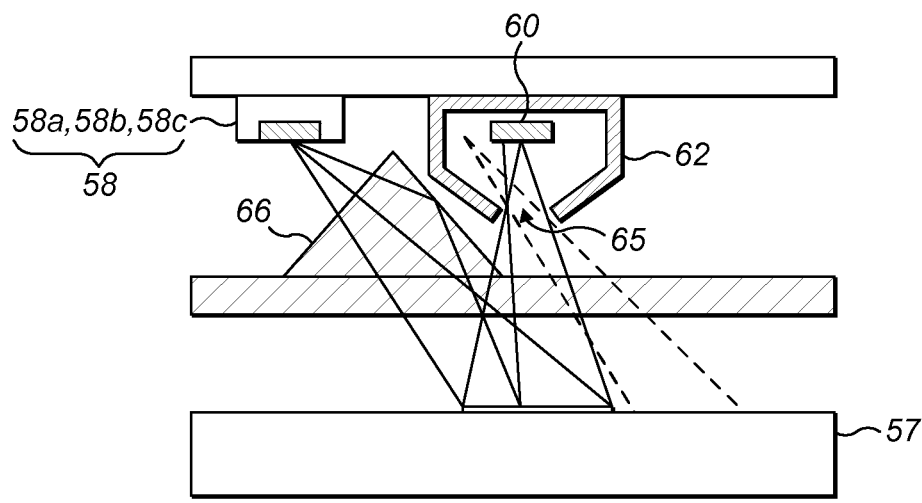
Figure 11:
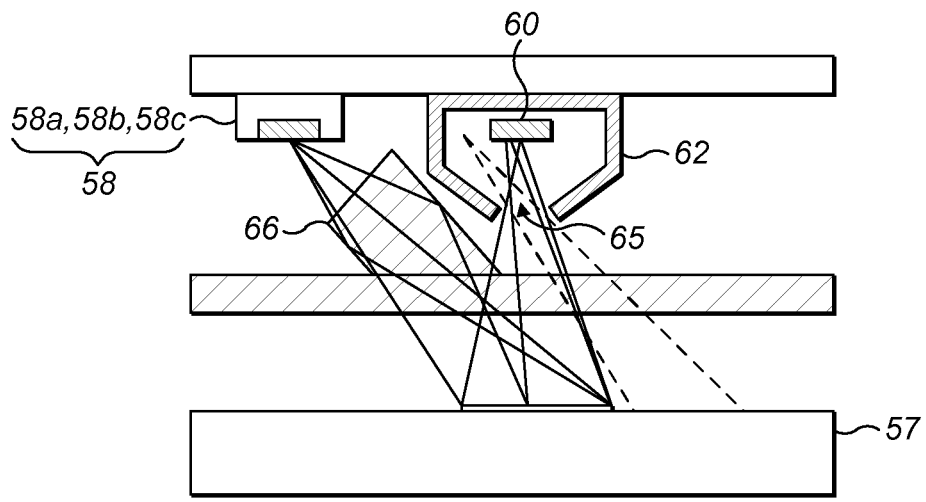

The heretofore mentioned aperture 65 has been described up to now as being defined by a shield 62 provided on the protection window 61. However this is not essential and the aperture 65 may instead be defined by a shield 62 that is not provided on the protection window 61. Such a shield may extend at least partially around the sensor 60 and at least partially into the field of view thereof, thereby limiting said field of view. The shield section that partially extends into the field of view of the sensor 60 in this manner defines the aperture through which light reflected from the surface portion 57 may travel onto the sensor. An example of one such shield arrangement is denoted 62 in FIGS. 10 and 11. The aperture 65 defined by the shield 62 in these figures may be circular, for instance. It will be appreciated that shields of the kind mentioned in this paragraph are also opaque to light of substantially all wavelengths detectable by the sensor 60 and may be coloured black and optionally may be matt.

Furthermore, although a shield 62 which defines an aperture 65 improves the reliability of reflection characteristics analysis implementable by a supplemental device 34, the provision of such a shield 62 (whatever the configuration thereof) is not essential to the invention hereafter claimed. In particular a supplemental device 34 that is not provided with a shield 62 will still function, provided that light from the light sources 58 cannot enter the sensor 60 without having been reflected from the surface 57 in use, albeit the reliability of reflection characteristics analysis implementable thereby will be less than if a shield 62 defining an aperture 65 were provided.

In some embodiments the secondary optical sensor unit 56 comprises a plurality of different sensors 60 (for example, a plurality of photodiodes). However each such sensor is additionally provided with a filter configured to filter incident light such that only light of a particular wavelength (or range of wavelengths) is detected by the sensor. In such an embodiment the secondary optical sensor unit 56 comprises one or more sensors configured to detect reflected light of the first wavelength $\lambda_1$. The secondary optical sensor unit 56 also comprises one or more sensors configured to detect reflected light of the second wavelength $\lambda_2$. The secondary optical sensor unit 56 further comprises one or more sensors configured to detect light of the third wavelength $\lambda_3$. In this embodiment the processor 40 causes the first to third light sources 58a to 58c (or groups thereof) to concurrently emit light of the first to third wavelengths $\lambda_1$ to $\lambda_3$ onto the surface portion 57 in use. This provides that first to third signals similar to those heretofore described (i.e. first to third signals S1 to S3) are generated concurrently.

In the embodiment outlined in the previous paragraph, although the respective exposure times for light of different wavelengths elapse concurrently, such exposure times may be of different durations. This is for calibration purposes. Specifically, this is such that if a surface portion 57 (or at least the part thereof from which light reflects onto the sensors) is a neutral colour (e.g. grey), then the signals generated by the respective sensors in response to detecting light of the different wavelengths are substantially similar. More specifically in this situation the signals generated by the respective sensors, which are indicative of the intensity of reflected light of respective wavelengths during respective exposure times, are substantially similar.

However, as has already been mentioned, calibrating a supplemental device 34 may alternatively involve adding or subtracting a factor to/from each of the values A to C such that the resulting values are substantially similar when the surface portion 57 being analysed is a neutral colour (e.g. grey). Calibrating in this manner enables the respective exposure times for light of different wavelengths to elapse concurrently, and for the respective exposure times to be substantially similar in duration.

In some embodiments the supplemental device 34 may be configured such that, in use, an optical path does not extend directly between the surface portion 57 and the sensor 60. For instance light may be reflected from the surface portion 57, through the aperture 65, and then redirected by a reflective surface (e.g. a mirror) onto the sensor 60. In such embodiments an optical path does not extend directly between the surface portion 57 and the sensor 60. Instead the optical path extends indirectly between the surface portion 57 and the sensor 60 via the one or more reflective surfaces (e.g. mirrors). Nevertheless the aperture 65 defined by the shield 62 may be located on this optical path and such that it restricts the amount of light which may be reflected from the surface portion 57 under analysis along the optical path and onto the sensor 60.

Figure 12:
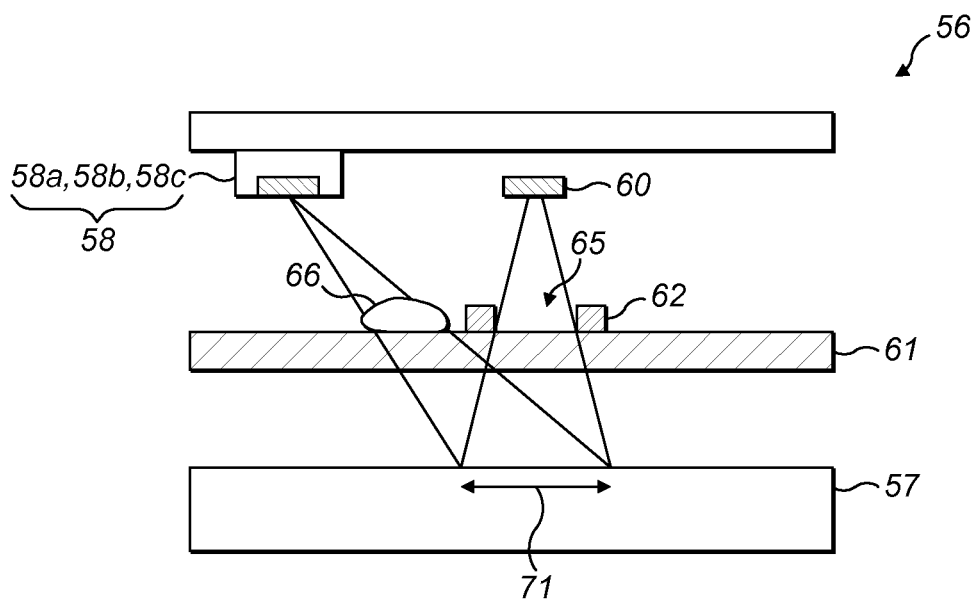

Now with reference to FIG. 12, in some embodiments the light guide may comprise a lens 66 which may comprise optics grade glass or plastic for instance. This lens 66 directs light from the light sources 58 onto the surface portion 57 in the field of view 71 of the sensor. The light sources 58 are tilted or aimed towards the lens 66 such that light from the light sources 58 is directed into the lens 66 which increases the intensity of light from the light sources that becomes incident on the relevant part of the surface portion 57. Advantageously, this improves the efficiency of the reflection characteristics analysis implementable by the supplemental device 34. The lens 66 should be provided in contact with the window 61 such that light is redirected by the lens 66 directly into the window 61, or alternatively the lens 66 may comprise an integral part of the window 61. For instance part of the window 61 may be formed such that it performs the function of the lens 66, and the light sources 58 may be tilted or aimed towards this part of the window 61.

Although it has been described that the reflection response of more than one wavelength of light is used to determine a property of an injection device, it is envisaged that in some other embodiments a parameter (e.g. a property of an injection device) may be determined by analysing the reflection response of a single wavelength of light, for instance by performing an analysis on the basis of signal S1 only. It will be appreciated that in such embodiments the secondary optical sensor unit 56 may only have a single light source, e.g. light source 58*a*. Persons skilled in the art will be familiar with how data collected during such an analysis may be processed to make such a determination.

Lastly, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

The invention claimed is:

1. An apparatus comprising:
 a sensor configured to generate a sensor output dependent on an intensity of light incident on the sensor, and the sensor having a field of view directed at an external surface in use;
 an illumination source configured to emit multichromatic light onto the external surface in use;
 an optically transparent window located such as to allow light to pass from the illumination source to the external surface and to allow light to pass to the sensor from the external surface in use;
 a light concentrator fixed to or integral with the window, the light concentrator being configured to concentrate at least some light from the illumination source onto the external surface in use such that the concentrated light is reflected from the external surface onto the sensor via the window, wherein the light concentrator comprises a light guide that is configured such that in use at least some light from the illumination source is reflected from an internal boundary surface of the light guide towards the external surface; and
 a processor configured to use the sensor output to determine information associated with reflection characteristics of the external surface.

2. The apparatus of claim 1, wherein the light guide is configured such that in use at least some light from the illumination source is internally reflected within the light guide towards the external surface.

3. The apparatus of claim 1, wherein the light guide comprises a plurality of surfaces arranged to reflect light from the illumination source towards the external surface.

4. The apparatus of claim 1, wherein the light concentrator is at least partially prismatic in shape.

5. The apparatus of claim 1, wherein at least part of the light concentrator has a substantially triangular shaped cross section.

6. The apparatus of claim 1, wherein the light concentrator has an optical power.

7. The apparatus of claim 6, wherein the light concentrator comprises a lens.

8. The apparatus of claim 1, wherein the apparatus is a supplemental device configured for attachment to an injection device.

9. The apparatus of claim 1, wherein the information comprises a property of an injection device which comprises the external surface.

10. The apparatus of claim 1, wherein the information comprises an indication of a type of medicament within an injection device which comprises the external surface.

11. The apparatus of claim 1, comprising a shield positioned between the sensor and the external surface, the shield defining an aperture that forms a field of view of the sensor on the external surface, wherein the field of view includes a region of the external surface illuminated by the illumination source.

12. The apparatus of claim 11, wherein the aperture is configured to allow only light that has been emitted by the illumination source and reflected by the external surface to become incident on the sensor.

* * * * *